United States Patent [19]
Mattler

[11] Patent Number: 4,572,181
[45] Date of Patent: Feb. 25, 1986

[54] CLAMPING/CUTTING APPARATUS

[76] Inventor: Martin Mattler, 3880 Franklin Rd., Bloomfield Hills, Mich. 48013

[21] Appl. No.: 589,765

[22] Filed: Mar. 15, 1984

[51] Int. Cl.$^4$ .................. A61B 17/12; A61B 17/32
[52] U.S. Cl. .................................. 128/305; 128/325; 128/346
[58] Field of Search ............... 128/346, 318, 305, 325, 128/334 R, 326; 227/DIG. 1

[56] References Cited

U.S. PATENT DOCUMENTS

| | | | |
|---|---|---|---|
| 3,006,344 | 10/1961 | Vogelfanger | 128/346 X |
| 3,175,556 | 3/1965 | Wood et al. | 128/305 |
| 3,545,444 | 12/1970 | Green | 227/DIG. 1 X |
| 4,273,129 | 6/1981 | Boebel | 227/DIG. 1 X |
| 4,428,374 | 1/1984 | Auburn | 128/318 |

Primary Examiner—Michael H. Thaler
Attorney, Agent, or Firm—Irving M. Weiner; Joseph P. Carrier; John J. Cantarella

[57] ABSTRACT

An apparatus for clamping and severing an umbilical cord or other elongated member, wherein a pair of clamps are held and positioned by a clamp carrier. A separate plunger member having severing blades mounted thereon operably cooperates with the clamp carrier by being received for slidable translation therein to effect severing. As the plunger is slid forwardly for severing operation, the pair of clamps are automatically released from the clamp carrier. The severing blades remain safely contained at all times within the clamp carrier throughout the operation.

12 Claims, 5 Drawing Figures

CLAMPING/CUTTING APPARATUS

BACKGROUND OF THE INVENTION

1. Field of the Invention

The present invention relates to an apparatus for clamping and severing an elongated member, and methods of constructing and utilizing such apparatus. More particularly, the invention relates to an apparatus for clamping and severing flexible and/or deformable members, such as an umbilical cord.

The phraseology "elongated member" as employed herein is intended to connote an umbilical cord, an artery, a vein, a capillary, a conduit, a tube, a duct, and generally any flexible and/or deformable member capable of being clamped and severed. Although the present invention will be hereinafter described in connection with the clamping and severing of an umbilical cord, the invention is not limited to use in connection with umbilical cords and may, for example, be applied for use in connection with clamping and cutting of any of the aforementioned members.

2. Description of Relevant Art

In standard child birth procedures, it is required that the doctor very carefully perform the delicate operation of cutting the umbilical cord at a point very close to the baby's abdomen. Heretofore, various attempts have been made to provide a device for clamping the umbilical cord and severing same such that the severed ends are separated and clamped. An exemplary device of such type is disclosed in U.S. Pat. No. 4,026,294 issued May 31, 1977 to the present inventor. Such device effectively attains the desirable object of avoiding any direct handling of the clamping members by employing the leverage of scissors for the clamping operation. Thereafter, the scissors are released from connection with the clamping members and are employed in a separate severing step.

Other combination umbilical clamp and cutting devices are disclosed in U.S. Pat. No. 3,106,919 issued Oct. 15, 1963 and U.S. Pat. No. 3,323,208. However, such devices are difficult to manipulate and have other attendant disadvantages. For example, such devices have a tendency to slip, especially when being handled by wet gloves or hands. Such slip problem is not alleviated by providing the outer clamp surfaces with non-slip formations, and is further accentuated by the lack of leverage provided by such devices. In this respect, considerable leverage is required in order to securely clamp and sever the umbilical cord. Further, such devices must be oriented so that the clamp side having the blade remains on the mother's side (i.e., the placenta side) of the cord for discarding with the placenta. A misorientation of such a device may injuriously leave the clamp side with the blade on the child's side of the cord, possibly resulting in infection and various other complications.

Other known devices for performing clamping and cutting operations include the circumcision instruments disclosed in U.S. Pat. No. 3,566,873 issued Mar. 2, 1971 and U.S. Pat. No. 3,706,312 issued Dec. 19, 1972; and the surgical instruments disclosed in U.S. Pat. No. 1,918,700 issued July 18, 1933 and U.S. Pat. No. 3,175,556 issued Mar. 30, 1965. However, such other known devices have generally failed to meet the desideratum for a clamping/cutting apparatus which may be easily and effectively employed in clamping and severing an umbilical cord, for example, while overcoming the foregoing problems.

The present invention overcomes each of the foregoing problems associated with known devices, and discloses a clamping/cutting apparatus which is even easier and more convenient to use than the device disclosed in the aforesaid U.S. Pat. No. 4,026,924 issued to the present inventor.

SUMMARY OF THE INVENTION

The present invention for clamping and severing an elongated member, comprising first and second means for clamping the elongated member, and third means operably and releasably interconnected to the first and second means for maintaining same in a predetermined side-by-side relationship and for moving the first and second clamping means to closed positions thereof wherein the elongated member is clamped by the first and second clamping means. The apparatus further includes fourth means for severing the clamped elongated member upon movement of the fourth means relative to the third means, the fourth means operably cooperating with the third means so as to be positioned thereby in relation to the first and second clamping means. The fourth means is integrally provided with fifth means for disconnecting the first and second clamping means from the third means upon movement of the fourth means to sever the clamped elongated member.

In a preferred embodiment, the third means comprises an elongated clamp carrier having an elongated opening for receiving the first and second clamping means and having a hinged upper part movable between opened and closed positions. The fourth means comprises a plunger member adapted to be slidably received through an open rear mouth portion of the clamp carrier, the plunger member having severing means provided at a forward portion thereof for severing the clamped elongated member upon forward sliding movement of the plunger member within the elongated opening of the clamp carrier, i.e., defining a syringe-like operable cooperation between the clamp carrier and plunger member. The fifth means comprises a pair of side flanges integrally formed on the plunger member for pushing the first and second clamping means out from the clamp carrier when the plunger member is moved forwardly to sever the clamped elongated member.

It is an object of the present invention to provide a combination clamping/cutting apparatus which affords sufficient clamping leverage for application to an umbilical cord, while avoiding any direct manual handling of the clamps themselves.

Another object of the present invention is to greatly facilitate the severing operation of an elongated member such as an umbilical cord by means of a severing action performed by sliding a plunger-like member within a clamp carrier, which member at the same time releases a pair of clamps from connection with the clamp carrier. Further, the severing means itself remains protectively confined within the clamp carrier when severing has been completed, thus avoiding possible injury to the baby or the operator.

A further object of the invention is to provide a clamping and cutting device which can be used from either side of an umbilical cord, while eliminating any hazard with respect to misorientation of a severing blade.

The above and further objects, details and advantages of the present invention will become apparent from the following detailed description of preferred embodiments of the invention, when read in conjunction with the accompanying drawings.

DETAILED DESCRIPTION OF PREFERRED EMBODIMENTS

Figure 1:
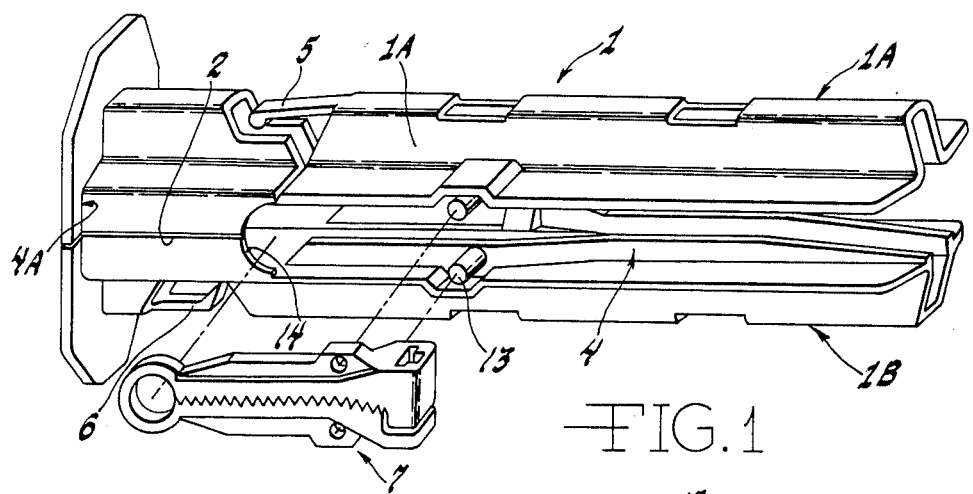
FIG. 1 depicts a perspective view of a clamp carrier and associated clamp in accordance with the invention.

With reference to the drawings, there is shown an apparatus for clamping and severing an elongated member, such as an umbilical cord. As shown in FIG. 1, the apparatus includes an elongated clamp carrier 1. The clamp carrier 1 includes an upper portion 1A and a lower portion 1B which are integrally connected (such as by ultrasonic welding) along a rear seam line 2. Such interconnection of the upper and lower portions 1A, 1B may be facilitated and strengthened by means of pin holes 3 provided in upper portion 1A (FIG. 3) adapted to mate with corresponding pins (not shown) provided in lower portion 1B, for example. The clamp carrier 1, as well as other main components of the invention described hereinbelow, is preferably formed of a strong and rigid material such as plastic or the like, and in a preferred embodiment various parts are formed of a white polypropylene material.

The upper and lower portions 1A, 1B of clamp carrier 1 have defined therein a common elongated opening 4. As shown in FIG. 1, the opening 4 is coextensive with the length of clamp carrier 1, i.e., it extends from the forward end to an open rear mouth portion 4A having a flange formed therearound. The upper portion 1A of clamp carrier 1 includes a forwardly opening hinged part 1A' which is pivotably movable relative to lower portion 1B between an open position (shown in broken line in FIG. 3) and a closed position (solid line in FIG. 3), as discussed in greater detail hereinbelow. The clamp carrier 1 is also provided with an upper locking mechanism 5 and a lower locking mechanism 6, also described in greater detail hereinbelow.

Figure 4:
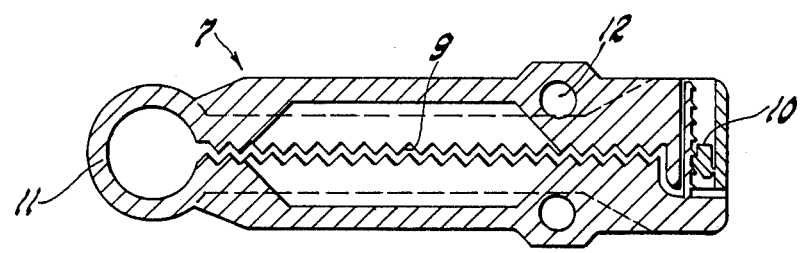
FIG. 4 shows a sectional view of a clamp in accordance with the invention.
Figure 5:
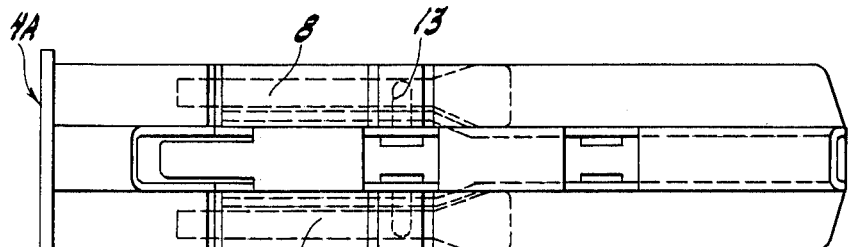
FIG. 5 depicts a top plan view of the clamp carrier of FIG. 1, having a pair of clamps as shown in FIG. 4 disposed therein.

As shown in FIGS. 1, 4 and 5, the clamping and severing apparatus according to the invention further comprises first and second clamping means in the form of a pair of substantially identical clamps 7 and 8 for clamping the umbilical cord or other elongated member. As shown in FIGS. 1 and 4 with respect to clamp 7, each of the clamps are provided with staggered teeth 9 which mesh when closed. Each clamp 7 and 8 is also provided with a releasable ratchet mechanism 10 including a catch integrally provided on a forward end of one of the jaws of the clamp for mating with ratchet steps integrally provided on a forward end of the other jaw of the clamp, the mechanism 10 providing automatically adjusting closing pressure on any size umbilical cord. The clamps 7, 8 may be fabricated of plastic or any other suitable material.

The clamps 7, 8 are each provided with a rear hinge portion 11 which normally biases the clamp 7 or 8 to be open in a free position. In a preferred embodiment, when the clamps are open in a free position, the planes of the tips of the teeth 9 form a dihedral angle of not less than 90°, for example. On the other hand, when the clamps 7, 8 are in their closed positions, the respective jaws thereof are positioned such that the staggered teeth 9 are in substantially close meshing cooperation, and the front ratchet mechanism 10 releasably locks the jaws in such closed position while automatically adjusting the closing pressure, depending on the size of the umbilical cord.

The clamps 7, 8 are adapted to be received on respective opposite sides in spaced side-by-side relationship within the elongated opening 4 of clamp carrier 5, as shown in dashed line in FIG. 5. On each side of the clamp carrier 1 are provided two dowel pins 13 (FIGS. 1 and 5), one on each of the upper and lower portions 1A, 1B. The clamps 7 and 8 are provided with a corresponding pair of dowel pin holes 12 adapted to mate with the dowel pins 13 so as to position the clamps 7 and 8 in their proper orientation within the clamp carrier 1. On each side of clamp carrier 1, the upper and lower portions 1A, 1B together define a curved recess 14 adapted to mate with the outer contour of hinge 11 of the clamps 7, 8, thus further aiding to properly position the clamps 7, 8 when they are disposed in side-by-side spaced relationship within the clamp carrier 1.

Figure 2:
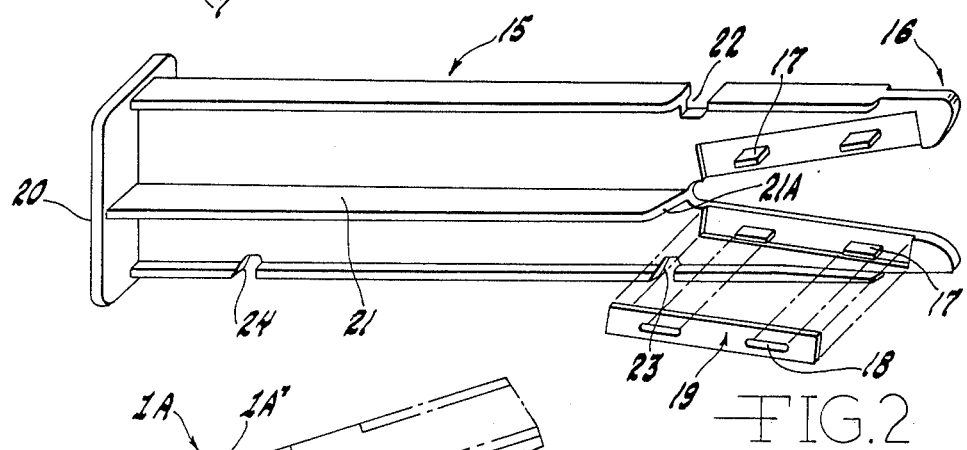
FIG. 2 depicts a perspective view of a plunger member with severing means in accordance with the invention.

The apparatus according to the invention further comprises a plunger member 15 as shown in FIG. 2. The plunger member 15 is substantially elongated, and is dimensioned and shaped so as to be substantially closely slidably received within the elongated aperture 4 of the clamp carrier 1, by insertion of the forward end of plunger 15 through the open rear mouth portion 4A of clamp carrier 1. The plunger 15 is formed with a bifurcated forward end 16 defining an angular opening. A pair of rectangular pins 17 are formed on each side of such angular opening, and are adapted to mate with corresponding rectangular apertures provided in a stainless steel blade 19. A pair of the stainless steel blades 19 are positioned on the forward bifurcated end 16 of plunger 15 to define the severing means for severing the umbilical cord or other elongated member. When fixed in position on bifurcated end 16 via the pins 17 and apertures 18, the stainless steel blades 19 have their cutting edges disposed in opposing relation within a forwardly opening V-shaped angle defined therebetween, thus providing for easy and sure severing of the umbilical cord.

The plunger 15 further includes a rear wall 20 which facilitates pushing of the plunger 15 within clamp carrier 1 in a manner to be described hereinbelow. Extending from the rear wall 20 forwardly to a position just rearwardly of the severing means provided on bifurcated end 16 are a pair of opposite side flanges 21 (only one shown in FIG. 2) having tapered forward ends 21A. The flanges 21 comprise means for disconnecting the clamps 7 and 8 from the clamp carrier 1 in a manner to be described subsequently.

As also shown in FIG. 2, plunger 15 is formed with a forward upper stop 22, a forward lower stop 23 and a rear lower stop 24, each of the stops 22, 23, 24 comprising a slot formed in the respective upper and lower elongated walls of the plunger 15. The stops 22, 23, 24 perform positioning functions of the plunger 15 relative to clamp carrier 1 as described hereinbelow.

Operation of the clamping and severing apparatus in accordance with the invention will now be described hereinbelow with reference to the foregoing description as well as the drawings.

Preferably, the clamp carrier 1 is shipped for use with the clamps 7, 8 positioned therein for space saving purposes as well as for the convenience of the doctor when he picks up the apparatus for use. Also, the forward end 16 of plunger 15 is preferably pre-inserted through the rear open mouth 4A of clamp carrier 1, the plunger 15 being received within clamp carrier 1 in a position in which the forward upper and lower stops 22, 23 of plunger 15 are respectively engaged by the upper and lower locking mechanisms 5, 6 of clamp carrier 1, so that the apparatus is entirely assembled and ready for use. It is to be noted in this respect that the angularly disposed cutting blades 19 on birfurcated end 16 of plunger 15 perform their severing action only at the rearmost closely disposed portions thereof (e.g., in the rear $\frac{1}{4}''$ thereof). Thus, when the plunger 15 is positioned in the foregoing manner, although the opposite legs of bifurcated end 16 will extend over a portion of the clamp carrier 1 wherein clamps 7, 8 are accommodated, the rear severing portions of the blades 19 will be positioned rearwardly of the clamps 7, 8.

Figure 3:
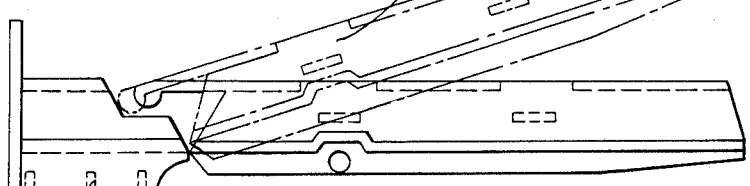
FIG. 3 illustrates a side elevational view of a top half of the clamp carrier of FIG. 1.

When the doctor desires to clamp and cut the umbilical cord or other elongated member, the hinged part 1A' of upper portion 1A of clamp carrier 1 is pivoted upwardly to the dashed line open position thereof shown in FIG. 3. At the same time, the ratchet locking mechanisms 10 of each of the clamps 7, 8 are released to permit the jaws 7, 8 to move their normally biased open positions. With the upper hinged part 1A' of clamp carrier 1 and the clamps 7, 8 thus in the open positions thereof, the doctor moves the apparatus into position such that the umbilical cord is disposed between the opposite open jaws of the clamps 7, 8. The forward end of hinged part 1A' of clamp carrier 1 is then pressed to its closed position, which in turn causes the clamps 7, 8 to close and their ratchet mechanisms 10 to lock. The staggered teeth 9 of each of the clamps 7, 8 firmly and securely clamp the umbilical cord therebetween, but without breaking or damaging the clamped cord.

After the cord has been clamped, the doctor pushes the plunger 15 forwardly within elongated opening 4 of clamp carrier 1, which causes the upper and lower locking mechanisms to release their engagement with stops 22, 23. As the plunger 15 is thus moved forwardly in a syringe-like operational cooperation with clamp carrier 1, the severing means defined by the fixed blades 19 passes between the clamps 7 and 8 to sever the umbilical cord. At the same time, forward movement of the plunger 15 causes the opposing flanges 21 to come into contact with the inner sides of each of the clamps 7, 8 so as to push the clamps respectively outwardly from the sides of opening 4 of clamp carrier 1. The clamps 7, 8 are thus automatically released from engagement with dowel pins 13 so as to be entirely free of clamp carrier 1 upon forward severing movement of plunger 15 within clamp carrier 1.

From the foregoing it will be understood that the doctor or other operator is never required to directly handle the clamps 7, 8 by virtue of the clamp carrier 1, which also provides a leverage action which facilitates effective clamping by clamps 7, 8 disposed therein. Further, the positioning of the blades 19 on plunger 15 within clamp carrier 1 provides for very safe, accurate and highly effective severing of the umbilical cord or other elongated member. In this respect it is to be noted that when severing action by blades 19 has been completed, the forward movement of plunger 15 within opening 4 of clamp carrier 1 is stopped when the rear stop 24 of plunger 15 is engaged by lower locking mechanism 6 provided on clamp carrier 1. In this position, the plunger 15 with the severing means is safely entirely contained within the clamp carrier 1, eliminating any risk of exposed cutting surfaces causing injury to the baby, mother or operator.

Another very important advantage attained by the apparatus according to the invention is the automatic disconnection of the clamps 7 and 8 when the plunger 15 is moved to sever the umbilical cord. By virtue of such arrangement, once the umbilical cord has been severed, the severed ends thereof are clamped to prevent bleeding, and the clamp on the mother's side of the severed cord can be merely discarded with the afterbirth. The clamping remaining on the baby can of course be removed at any suitable later time simply by releasing the ratchet mechanism 10 from its locked position. In this respect it is to be noted that the ratchet mechanism 10 permits adjustment and re-positioning of the clamp remaining on the baby, to accommodate changes in the size of the cord, etc.

It will be understood that the apparatus in accordance with the invention permits rapid, convenient and safe clamping and severing of the umbilical cord during child birth, and eliminates any need for separate and distinct clamping and severing procedures and tools. It will also be evident from the foregoing description that the novel apparatus and method in accordance with the invention clearly satisfies all of the objects of the invention, as well as others, including many advantages of great practical utility and commercial importance.

Although there have been described what are at present considered to be the preferred embodiments of the invention, it will be understood that the present invention may be embodied in other specific forms without departing from the spirit or essential characteristics thereof. The present embodiments are therefore to be considered in all respects as illustrative and not restrictive. The scope of the invention is indicated by the appended claims.

I claim:

1. An apparatus for clamping and severing an elongated member, comprising:
   first means for clamping said elongated member;
   second means for clamping said elongated member;
   third means operably and releasably interconnected to said first and second means for maintaining said first and second clamping means in a predetermined side-by-side relationship and for moving said first and second clamping means to closed positions thereof wherein said elongated member is clamped by said first and second clamping means;
   fourth means for severing said clamped elongated member upon movement of said fourth means relative to said third means, said fourth means operably cooperating with said third means so as to be positioned thereby in relation to said first and second clamping means; and
   said fourth means being integrally provided with fifth means for disconnecting said first and second clamping means from said third means upon movement of said fourth means to sever said clamped elongated member.

2. An apparatus according to claim 1, wherein:
said third means comprises an elongated clamp carrier including upper and lower portions; and
said upper and lower portions have a common elongated opening defined therein for receiving said first and second clamping means in spaced side-by-side relationship.

3. An apparatus according to claim 2, wherein:
said upper portion of said clamp carrier includes a forwardly extending hinged part which is pivotably movable relative to said lower portion of said clamp carrier between an open position, wherein said first and second clamping means may be received in said common opening in open positions thereof, and a closed position wherein said first and second clamping means are moved to said closed positions thereof; and
said first and second clamping means are provided with automatically adjusting lock mechanisms.

4. An apparatus according to claim 3, wherein:
said common elongated opening defined in said upper and lower portions of said clamp carrier extends through to a rear end of said clamp carrier so as to define an open rear mouth portion;
said fourth means comprises a plunger member adapted to be slidably received through said open rear mouth portion of said clamp carrier and slidably translated within said elongated opening of said clamp carrier; and
said plunger member has severing means provided at a forward portion thereof for severing said clamped elongated member upon forward sliding movement of said plunger member within said elongated opening of said clamp carrier.

5. An apparatus according to claim 4, wherein:
said severing means comprises a pair of cutting blades releasably mounted in fixed opposing positions on said forward portion of said plunger member so as to be in forwardly open angular relation to each other.

6. An apparatus according to claim 4, wherein:
said plunger member is slidably received in said elongated opening of said clamp carrier such that said severing means passes between said first and second clamping means upon forward movement of said plunger member in said clamp carrier.

7. An apparatus according to claim 4, wherein:
said plunger member is provided with a plurality of stops, at least one of said stops being provided proximal a rear portion of said severing means and at least a second one of said stops being provided at a rear portion of said plunger member; and
said clamp carrier is provided at a substantially rear portion thereof with at least one position locking mechanism which cooperates with said at least one stop to retain said plunger member in a rearward position within said clamp carrier, and which cooperates with said second stop to retain said plunger member in a forward position within said clamp carrier.

8. An apparatus according to claim 7, wherein:
said upper portion of said clamp carrier includes a forwardly extending hinged part which is pivotably movable relative to said lower portion of said clamp carrier between an open position, wherein said first and second clamping means may be received in said common opening in open positions thereof, and a closed position wherein said first and second clamping means are moved to said closed positions thereof;
said clamp carrier is provided with at least a pair of dowel pins for releasably holding said first and second clamping means in position within said common opening of said clamp carrier; and
said first and second clamping means are provided with automatically adjusting lock mechanisms.

9. An apparatus according to claim 8, wherein:
said common elongated opening defined in said upper and lower portions of said clamp carrier extends through to a rear end of said clamp carrier so as to define an open rear mouth portion;
said fourth means comprises a plunger member adapted to be slidably received through said open rear mouth portion of said clamp carrier and slidably translated within said elongated opening of said clamp carrier; and
said plunger member has severing means provided at a forward portion thereof for severing said clamped elongated member upon forward sliding movement of said plunger member within said elongated opening of said clamp carrier.

10. An apparatus according to claim 9, wherein:
said plunger member is integrally provided with means for disconnecting said first and second clamping means from said clamp carrier upon movement of said plunger member to sever said clamped elongated member.

11. An apparatus for clamping and severing an elongated member, comprising:
first means for clamping said elongated member;
second means for clamping said elongated member;
third means operably and releasably interconnected to said first and second means for maintaining said first and second clamping means in a predetermined side-by-side relationship and for moving said first and second clamping means to closed positions thereof wherein said elongated member is clamped by said first and second clamping means;
fourth means for severing said clamped elongated member upon movement of said fourth means relative to said third means, said fourth means operably cooperating with said third means so as to be positioned thereby in relation to said first and second clamping means;
said fourth means being integrally provided with fifth means for disconnecting said first and second clamping means from said third means upon movement of said fourth means to sever said clamped elongated member;
said third means comprises an elongated clamp carrier including upper and lower portions;
said upper and lower portions have a common elongated opening defined therein for receiving said first and second clamping means in spaced side-by-side relationship;
an upper portion of said clamp carrier includes a forwardly extending hinged part which is pivotably movable relative to said lower portion of said clamp carrier between an open position, wherein said first and second clamping means may be received in said common opening in open positions thereof, and a closed position wherein said first and second clamping means are moved to said closed positions thereof;

said common elongated opening defined in said upper and lower portions of said clamp carrier extends through to a rear end of said clamp carrier so as to defin an open rear mouth portion;

said fourth means comprises a plunger member adapted to be slidably received through said open rear mouth portion of said clamp carrier and slidably translated within said elongated opening of said clamp carrier;

said plunger member has severing means provided at a forward portion thereof for severing said clamped elongated member upon forward sliding movement of said plunger member within said elongated opening of said clamp carrier;

said fifth means comprises a pair of flanges extending in opposite sideward directions from said plunger member along a length of said plunger member extending from a rear portion thereof to a portion thereof disposed rearwardly of said severing means; and said first and second clamping means are positioned within said common opening of said clamp carrier so as to be pushed outwardly from said opening, and disconnected from said clamp carrier, by said flanges upon forward severing movement of said plunger member to sever said clamped elongated member.

12. An apparatus according to claim 11, wherein:

said clamp carrier is provided with at least a pair of dowel pins for releasably holding said first and second clamping means in position within said common opening of said clamp carrier.

* * * * *